US00PP18865P3

(12) United States Plant Patent
Layt

(10) Patent No.: US PP18,865 P3
(45) Date of Patent: Jun. 3, 2008

(54) ***PHORMIUM TENAX* PLANT NAMED 'PHORD1'**

(50) Latin Name: *Phormium tenax*
Varietal Denomination: PHORD1

(75) Inventor: Todd Anthony Layt, New South Wales (AU)

(73) Assignee: VersaScapes L.L.C., Mount Pleasant, SC (US)

( * ) Notice: Subject to any disclaimer, the term of this patent is extended or adjusted under 35 U.S.C. 154(b) by 55 days.

(21) Appl. No.: 11/501,292

(22) Filed: Aug. 9, 2006

(65) Prior Publication Data

US 2007/0061935 P1 Mar. 15, 2007

Related U.S. Application Data

(60) Provisional application No. 60/711,248, filed on Aug. 25, 2005.

(51) Int. Cl.
*A01H 5/00* (2006.01)

(52) U.S. Cl. ..... Plt./373

(58) Field of Classification Search ..... Plt./373
See application file for complete search history.

(56) References Cited

PUBLICATIONS

LAYT; "Phormium tenax 'PHORD1'" *Plant Varieties Journal* 17 (3): 23, 71 (Oct. 27, 2004).

*Primary Examiner*—Annette H Para
(74) *Attorney, Agent, or Firm*—Myers Bigel Sibley & Sajovec, P.A.

(57) ABSTRACT

'PHORD1' is a distinctive variety of *Phormium tenax* characterized by a medium growth habit with a medium shoot density when compared with common *Phormium tenax* which has a variable growth form ranging from short to tall plant height and sparse to dense shoot density. In addition, 'PHORD1' has a deep red leaf color, whereas common *Phormium tenax* has a purple leaf color. 'PHORD1' also has strong resistance to Phytophthora root rot, whereas common *Phormium tenax* has week resistance.

1 Drawing Sheet

Latin name of the genus and species: The Latin name of the novel variety disclosed herein is *Phormium tenax.*

Variety denomination: The inventive variety of *Phormium tenax* disclosed herein has been given the varietal denomination 'PHORD1'.

BACKGROUND OF THE INVENTION

The present invention relates to a new and distinct perennial variety of *Phormium tenax,* which has been given the varietal denomination of 'PHORD1'. Its market class is that of an ornamental plant. 'PHORD1' is intended for use in landscaping and as a decorative plant.

Parentage. The *Phormium tenax* variety 'PHORD1' was selected in an Australian nursery in the state of New South Wales following a selection process involving large quantities of common *Phormium tenax* production stock. 'PHORD1' is a seedling selection from common *Phormium tenax.* 'PHORD1' was selected due to its deep red leaf color and resistance to the plant pathogen Phytophthora, which causes Phytophthora root rot.

Asexual reproduction. 'PHORD1' was first propagated asexually by division in the state of New South Wales, Australia and has since been asexually propagated by division and micropropagation.

Divisions were made for several subsequent generations, and 'PHORD1' was observed to retain the characteristics that were noted in the original 'PHORD1' seedling. Thus, the distinctive characteristics of the inventive 'PHORD1' variety have remained stable and true to type from generation to generation through successive cycles of asexual reproduction.

An application for plant breeders' rights for variety 'PHORD1' has been filed with the Australian Plant Breeders' Rights Office, and was first gazetted in the Plant Varieties Journal under Application No. 2004/250.

SUMMARY OF THE INVENTION

'PHORD1' is a distinctive variety of *Phormium tenax* characterized by a medium growth habit with a medium shoot density when compared with common *Phormium tenax,* which has a variable growth form ranging from short to tall plant height and sparse to dense shoot density. In addition, 'PHORD1' has a deep red leaf color, whereas common *Phormium tenax* has a purple leaf color. 'PHORD1' also has strong resistance to Phytophthora root rot, whereas common *Phormium tenax* has weak resistance.

BRIEF DESCRIPTION OF THE FIGURE

The photograph in the drawing was made using conventional techniques and shows the colours as true as reasonably possible by conventional photography. Colours in the photograph may differ slightly from the colour values cited in the detailed botanical description, which accurately describe the colours of the new *Phormium tenax.*

BOTANICAL DESCRIPTION OF THE PLANT

Figure 1:
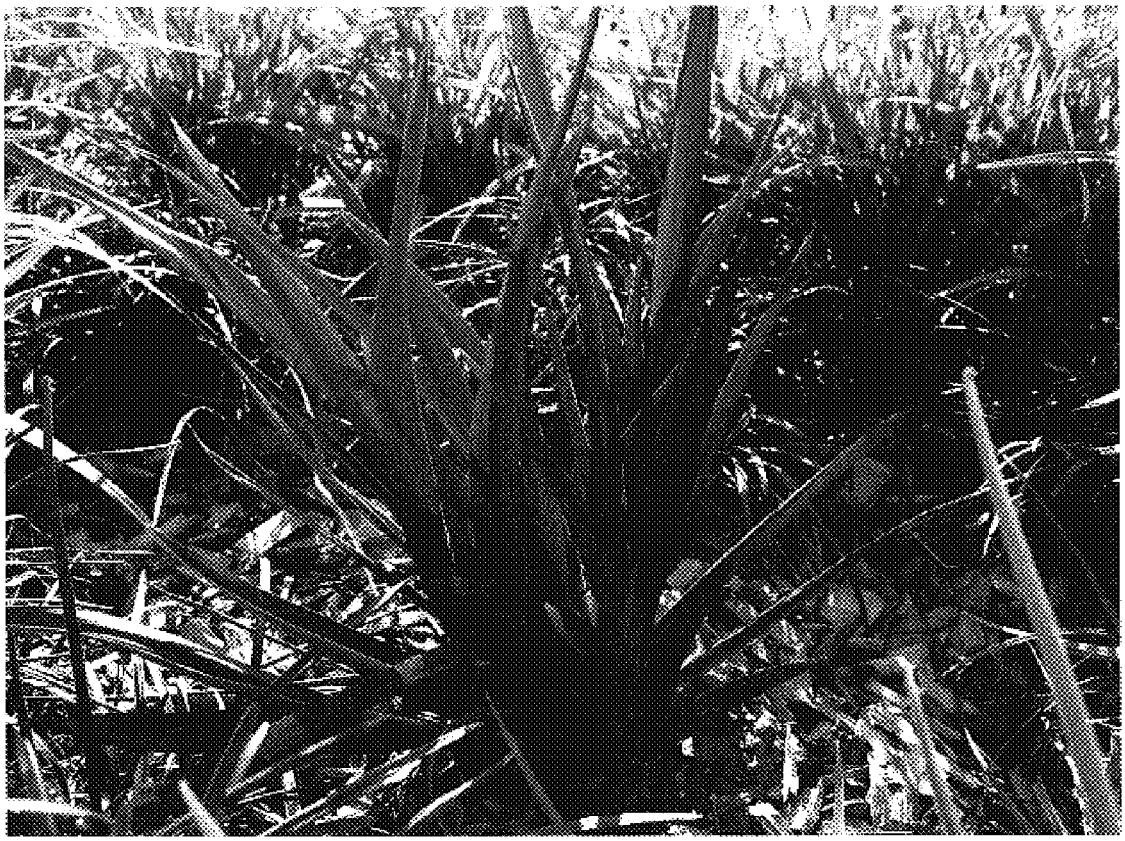
FIG. 1 shows an exemplary 'PHORD1' plant.

The following is a detailed botanical description of a new and distinct variety of a *Phormium tenax* ornamental plant known as 'PHORD1'. Plant observations were made on 14 month old plants grown in New South Wales, Australia.

Unless indicated otherwise, the descriptions disclosed herein are based upon observations made of mature 'PHORD1' plants grown in nursery pots and field plots.

Those skilled in the art will appreciate that certain characteristics will vary with older or, conversely, younger plants. 'PHORD1' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like. Color notations are based on The Royal Horticultural Society Colour Chart (The Royal Horticultural Society, London, 1995 edition).

'PHORD1' is a perennial *Phormium tenax* plant which is a seedling selection form a common *Phormium tenax* purple form. After its selection, 'PHORD1' was asexually propagated by division and then by micropropagation. 'PHORD1' has a deep red leaf color, which falls within the Royal Horticultural Society color grouping of greyed-purple, with no prominent contrasting coloration of the midrib and leaf margin. A botanical description of 'PHORD1' and a comparison with other varieties of *Phormium tenax* are provided below. A representative 'PHORD1' plant is shown in FIG. 1.

Technical Description of the Variety

Growth habit: 'PHORD1' is a medium, rhizomatous plant forming an upright fan-shaped tuft. Average plant height is 85–90 cm and average plant spread is 60 cm in a mature plant grown in a 300 mm nursery pot or a field plot in Sydney, New South Wales, Australia.

Leaves: The upper side of the leaf is greyed-purple (approximately RHS 187A) in color. The leaf margin and lower side midrib is greyed-purple in color (approximately RHS 183A). The leaf lower side is initially greyed-green (approximately RHS 191A) and changes to a reddish colour corresponding to the upper leaf side. The leaf is generally 40–42 mm in width, and reaches an average length of 50–60 cm. The leaf shape is linear-ensiform, the leaf base is cauline, the leaf margin is entire, the leaf apex is acute and the leaf surface texture is characteristised by fine striations. The leaf venation pattern is parallel and the venation color is the same as the rest of leaf (greyed-purple, approximately RHS 187A). The leaf attitude is erect. The color of the base of the shoot where the leaves unite is yellow-green (RHS144C-D).

Roots: The roots of 'PHORD1' are fleshy and thick, similar to other *Phormium tenax*.

Flowers: Flower development has not been observed on the new variety.

Environmental tolerances: 'PHORDI' has typical shade tolerance for the species. 'PHORD1' has been observed to hold color to −8 degrees Celsius without any noticeable change in appearance of the plant. 'PHORD1' has moderate to good drought tolerance. 'PHORD1' has moderate to good recovery with watering after severe wilting. 'PHORD1' does well in sandy soils, but also tolerates heavy, clay-type soils well.

Disease resistance: 'PHORD1' has excellent resistance to Phytophthora root rot compared to other similar *Phormium tenax* cultivars.

These features and other characteristics of the plant are apparent from figure.

Comparison of PHORD1 with Other Varieties of *Phormium tenax*

'PHORD1' has a medium sized upright growth habit, medium shoot density and a redder leaf color combined with stronger resistance to Phytophthora root rot than common *Phormium tenax*.

'PHORD1' has a more reddish foliage color than common *Phormium tenax* and another comparable type of *Phormium tenax* known as 'Merlot' (U.S. Plant Pat. No. 14,228, issued to Woolmore) with a fully expanded upper side leaf color of greyed-purple (approximately RHS 187A), whereas common *Phormium tenax* is highly variable from greyed-green to greyed-purple and 'Merlot' has an upper side leaf color greyed-purple (approximately RHS 183A). 'PHORD1' has no prominent contrast between leaf margin or midrib and the rest of the leaf blade color, whereas 'Merlot' has a contrasting leaf margin and midrib that is black (RHS 202A). 'PHORD1' has also demonstrated a stronger resistance than 'Merlot' to the disease Phytophthora root rot when grown in nursery pots in Sydney, New South Wales, Australia.

In addition, 'PHORD1' differs from the variety of *Phormium tenax* 'Platt's Black' (unpatented) as 'PHORD1' has a more reddish foliage color, whereas 'Platt's Black' has a brown leaf color (approximately RHS 200A). 'PHORD1' also has a more upright growth habit than 'Platt's Black', which is more spreading to arching.

Further, 'PHORD1' differs from the variety 'Dark Delight' (unpatented) as 'PHORD1' has a more reddish foliage color, whereas 'Dark Delight' has a more purple leaf color. 'PHORD1' also has a yellow-green color at the base of the shoot where the leaves unite, whereas 'Dark Delight' has a more purple color.

'PHORD1' also differs from the variety 'Anna Red' (unpatented) as 'PHORD1' has a more reddish foliage color, whereas 'Anna Red' has a more greyed-green leaf color, with a red margin and lower side midrib color. In addition, 'PHORD1' has an upright growth habit and an average plant height of 85–90 cm, whereas 'Anna Red' is more spreading to arching and is taller in height (average 110 cm).

The combination of its greyed-purple leaf color, upright growth habit and strong disease resistance makes 'PHORD1' as desirable ornamental plant suited for mass production for pot and landscape use.

That which is claimed is:

1. A new and distinct variety of *Phormium tenax* plant named 'PHORD1', substantially as described and illustrated herein.

* * * * *